(12) United States Patent
Knauseder et al.

(10) Patent No.: US 6,465,233 B1
(45) Date of Patent: Oct. 15, 2002

(54) NUCLEIC ACID MOLECULE ENCODING A CEPHALOSPORIN ACETYLESTERASE

(75) Inventors: Franz Knauseder, Kirchbichl; Martin Schiestl, Kufstein; Kurt Schörgendorfer, Langkampfen, all of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/601,027

(22) PCT Filed: Jan. 27, 1999

(86) PCT No.: PCT/EP99/00521

§ 371 (c)(1),
(2), (4) Date: Jul. 26, 2000

(87) PCT Pub. No.: WO99/38982

PCT Pub. Date: Aug. 5, 1999

(30) Foreign Application Priority Data

Jan. 28, 1998 (AT) .............................................. 99906207

(51) Int. Cl.⁷ .............................. C12N 9/18; C12N 15/53
(52) U.S. Cl. ...................... 435/197; 435/51; 435/252.3; 435/320.1; 536/23.2
(58) Field of Search .............................. 435/197, 320.1, 435/252.3, 51; 536/23.2

(56) References Cited

FOREIGN PATENT DOCUMENTS

EP          0 454 478          10/1991

OTHER PUBLICATIONS

Abbott et al., Applied Microbiology, vol. 30(3), "Physical Properties and Kinetic Behavior of a Cephalosporin Acetylesterase Produced by *Bacillus subtilis*," pp. 413–419 (1975).

Higerd et al., Journal of Bacteriology, vol. 114(3), "Isolation of Two Acetyl Esterases from Extracts of *Bacillus subtilis*," pp. 1184–1192 (1973).

Konecny et al., Boichimica et Biophysica Acta, vol. 485, "Effects of Carrier Morphology and Buffer Diffusion on the Expression of Enzymatic Activity," pp. 367–378 (1977).

Konecny, J., Enzyme Engineering, vol. 4, pp. 253–259 (1979).

Pridmore Raymond D., Gene, vol. 56, "New and Versatile Cloning Vectors with Kanamycin–Resistance Marker," pp. 309–312 (1987).

Sanger et al., Proc. Natl. Sci. USA, vol. 74(12), "DNA Sequencing with Chain–Terminating Inhibitors," pp. 5463–5467 (1977).

Takimoto et al., Journal of Fermentation and Bioengineering, vol. 77(1), "Purification Characterization and Partial Amino Acid Sequences of a Novel Cephalosporin–C Deacetylase from *Bacillus subtilis*," pp. 17–22 (1994).

Chemical Abstracts XP–002103758, Thanomsub et al., vol. 125(13), No. 159786g (1996).

Thanomsub et al., Microb., Util. Renewable Resour., vol. Date 1995, 9, "Cloning of Cephalosporin C Acetylesterase Gene from *Bacillus subtilis* WRRL–B558," pp. 395–399 (1996).

Tsushima et al., Chem. Pharm. Bull., vol. 27(3), "A New Route to Semisynthetic Cephalosporins from Deacetylcephalosporin C. I. Synthesis of 3–Heterocyclicthiometyl––cephalosporins," pp. 696–702 (1979).

Yanisch–Perron et al., Gene, vol. 33, "Improved M13 phage cloning vectors and host strains: nucleotide sequences of the M13mp18 and pUC19 vectors," pp. 103–119 (1985).

*Primary Examiner*—Charles L. Patterson, Jr.
(74) *Attorney, Agent, or Firm*—Hesna J. Pfeiffer

(57) ABSTRACT

The present invention relates to a nucleic acid molecule which codes for the cephalosporin acetylesterase from *Bacillus subtilis* ATCC 6633 (DSM 11909), vectors and host cells which comprise such a nucleic acid molecule, a process for the recombinant preparation of cephalosporin acetylesterase from *B. subtilis* ATCC 6633 (DSM 1 1909) using said nucleic acid molecule, and a process for preparing 3-deacetylcephalosporin compounds.

9 Claims, No Drawings

# NUCLEIC ACID MOLECULE ENCODING A CEPHALOSPORIN ACETYLESTERASE

FIELD OF THE INVENTION

The present invention relates to a nucleic acid molecule which codes for the cephalosporin acetylesterase from *Bacillus subtilis* ATCC 6633 (DSM 11909), vectors and host cells which comprise such a nucleic acid molecule, a process for the recombinant preparation of cephalosporin acetylesterase from *B. subtilis* ATCC 6633 (DSM 11909) using said nucleic acid molecule, and a process for preparing 3-deacetylcephalosporin compounds.

BACKGROUND OF THE INVENTION

Cephalosporin C is cleaved by cephalosporin acetylesterase (CAE) to 3-deacetyl-cephalosporin C (see, for example, B. J. Abbott et al., Appl. Microbiol. (1975), 413–419; J. Konecny et al., Biochim. Biophys. Acta 485 (1977), 367–378). It is furthermore possible to convert the cephalosporin compound 7-aminocephalosporanic acid (7-ACA) with CAE to 7-amino-3-deacetylcephalosporanic acid (HACA). 3-Deacetylcephalosporin C and HACA are used as intermediates in preparation of semisynthetic cephalosporins (S. Tsushima et al., Chem. Pharmacol. Bull. 27 (1979), 696–702). Various cephalosporin acetylesterases from diverse *Bacillus subtilis* (*B. subtilis* hereinafter) strains have been disclosed in the literature (see T. B. Higherd et al., J. Bacteriol. 114 (1973), 1184–1192; B. J. Abbott et al., Appl. Microbiol. (1975), 413–419; A. Takimoto et al., J. Ferment. Bioeng. 77 (1994), 17–22). Another cephalosporin acetylesterase was isolated by J. Konecny et al. (see J. Konecny et al., Biochim. Biophys. Acta 485 (1977), 367–378) from the *B. subtilis* strain ATCC 6633. The last-mentioned cephalosporin acetylesterase is particularly suitable for carrying out the abovementioned conversions of cephalosporin C into 3-deacetylcephalosporin C and of 7-ACA into HACA.

It is desirable, for technical and commercial reasons, to prepare the CAE required for the said conversion by a recombinant route. In particular, it would be possible in this way to produce in a simple and cost-effective manner the amounts of CAE required for carrying out the conversion process industrially. However, it has not been possible to date to clone the nucleic acid sequence coding for the cephalosporin acetylesterase from *B. subtilis* ATCC 6633 (DSM 11909).

It is thus an object of the present invention to provide the nucleic acid sequence coding for the cephalosporin acetylesterase from *B. subtilis* ATCC 6633 (DSM 1 1909). It is a further object of the present invention to provide vectors, in particular expression vectors, which comprise this nucleic acid sequence, and host cells which comprise these vectors. It is a further object of the present invention to provide a recombinant process for preparing the said cephalosporin acetylesterase. Finally, it is an object of the present invention to provide a process for preparing 3-deacetylcephalosporin compounds using a recombinant cephalosporin acetylesterase from *B. subtilis* ATCC 6633 (DSM 11 909).

DETAILED DESCRIPTION OF THE INVENTION

It has surprisingly been possible within the scope of the present invention to establish the nucleic acid sequence codings for the cephalosporin acetylesterase from *B. subtilis* ATCC 6633 (DSM 11909).

One aspect of the present invention is thus a nucleic acid molecule which codes for the cephalosporin acetylesterase from *B. subtilis* ATCC 6633 (DSM 11909).

In this connection, the cephalosporin acetylesterase from *B. subtilis* ATCC 6633 (DSM 11909) essentially corresponds to the activity described by J. Konecny et al. (see above). In particular, J. Konecny et al. refer to a value of the Michaelis-Menten constant $K_m$ for the conversion of cephalosporin C into 3-deacetylcephalosporin C of about $K_m=15$ mM (at 25° C.).

The cephalosporin acetylesterase from *B. subtilis* ATCC 6633 (DSM 11909) is, in particular, a polypeptide which has the amino acid sequence shown in the sequence identity No. (abbreviated to SEQ ID NO. hereinafter) 1 which is reproduced in Annex 1.

The nucleic acid molecule according to the invention preferably comprises a base sequence of the SEQ ID NO. 2 depicted in Annex 2. Also preferred is a nucleic acid molecule according to the invention which has exclusively the base sequence shown in SEQ ID NO. 2. A nucleic acid molecule according to the invention is, in particular, in the form of a DNA, for example of a cDNA. However, the invention also relates to nucleic acid molecules having the said properties, for example, an RNA, for example an mRNA or a pre-mRNA.

A nucleic acid molecule according to the invention can be obtained in the following way:

(i) Chromosomal DNA is extracted from *B. subtilis* ATCC 6633 (DSM 11909), purified and prepared for subsequent amplification, for example with the aid of PCR experiments (PCR =polymerase chain reaction). Primers able specifically to hybridize with the 5' end or with the 3' end of the nucleic acid sequence depicted in SEQ ID NO. 2 are constructed. An example of a 5' primer which can be used is an oligonucleotide which corresponds to nucleotides Nos 1 to 27 in the nucleic acid sequence depicted in SEQ ID NO. 2. An example of a 3' primer which can be used is an oligonucleotide which is complementary to nucleotides Nos 93 i to 957 in SEQ ID NO. 2. It is possible and advantageous to provide one or more restriction cleavage sites in the primers for subsequent cloning. The primers are used to carry out a suitable amplification method, for example a PCR experiment. (ii) The result of the amplification, for example of the PCR, is analysed, for example by electrophoresis on an agarose gel. It is possible with the aid of the abovementioned primers to obtain DNA fragments which can be extracted from the agarose gel and cloned into suitable vectors, for example selective plasmid vectors. A vector obtained in this way can then be used to transform a suitable host cell or a suitable host organism. For example, the DNA fragments obtained in the preceding step are inserted into an *E. coli* cloning vector, and the resulting recombinant plasmid is introduced by transformation or electroporation into *E. coli* cells. To produce colonies, the transformants are plated out on agar medium with an antibiotic, which is appropriate for the plasmid vector used, as selection pressure. (iii) A few of the resulting clones are selected, and the base sequence of the DNA insert is established. For example, DNA of the recombinant plasmid is extracted from a large number of selected *E. coli* colonies and is analysed with restriction enzymes. Subsequently, as a check, the base sequence of the DNA fragment originating from *B. subtilis* is determined. For this purpose, the fragments from several independently isolated clones are sequenced in order to detect any mutations due to the process. The nucleic acid sequence which has been established, and the amino acid sequence derived therefrom, is then compared with the sequences depicted in SEQ ID NO. 2 and SEQ ID NO. 1, respectively, in order to find a nucleic acid sequence which is sought. The appropriate clone of the host cell can then be grown further, and the vector containing the nucleic acid molecule according to the invention and, finally, the nucleic acid molecule according to the invention itself can be isolated.

Particularly suitable host cells or host organisms are bacterial strains, for example, E. coli. It is possible and advantageous to use as E. coli host a strain of the E. coli derivative K2, for example, W3110, HB101, C600, JM87, JM103, JM105 or JM109. Examples of E. coli vectors which can be used for the cloning are both plasmid vectors such as pUC13, pK19, pBR322 and pAT153, and phage vectors, for example, lambda gt10. The abovementioned hosts and vectors are merely examples of many others which are commercially available and can be obtained straightforwardly.

Oligonucleotides can be synthesized using a commercially available DNA synthesizer in accordance with the manufacturer's instructions.

Determination of a nucleic acid sequence according to the invention can be carried out by the method of Sanger et at. (1977), employing a known M13 vector system, or a commercially available sequencing kit can be used. Alternatively, a nucleic acid sequence according to the invention can be established using an automated sequencer.

The recombinant processes described above for preparing a nucleic acid molecule according to the invention are familiar to the skilled person. In this connection, reference is made to the monograph by J. Sambrook et al. (Ed.), "Molecular Cloning" (1989), Cold Spring Harbor Laboratory Press.

Alternatively, a nucleic acid molecule according to the invention can also be prepared semisynthetically by known processes. For this purpose, for example, complementary nucleic acid fragments which overlap in the 5' or 3' region and have in each case a length of up to 250–300 nucleotides of SEQ ID NO.2 are prepared and hybridized together, and the gaps are filled in enzymatically. Double-stranded nucleic acid fragments obtained in this way are finally, where appropriate, ligated together (see, for example, H. lbelgaufts, "Gentechnologie von A bis Z" (1 990), VCH, Weinheim), A further aspect of the present invention relates to a vector which is compatible with a predetermined host cell, the vector comprising a nucleic acid molecule according to the invention. As described above, a vector of this type is, in a preferred embodiment, a cloning vector.

In a further preferred embodiment, a vector according to the invention is an expression vector. An expression vector of this type can be used in a process for the recombinant preparation of the cephalosporin acetylesterase from B. subtilis ATCC 6633 (DSM 11909), a process of this type representing a further aspect of the invention. A process of this type according to the invention comprises:

(i) a host cell which is transformed with an expression vector according to the invention being cultivated under conditions suitable for bringing about the expression of the cephalosporin acetylesterase and, where appropriate, (ii) the expressed cephalosporin acetylesterase being isolated.

To construct a recombinant expression vector, the nucleic acid fragment according to the invention, in particular a corresponding cDNA, is modified in a suitable manner for cloning and then introduced into a gene expression vector, for example an expression plasmid, so that the structural gene comes under the control of appropriate regulatory sequences, for example a suitable promoter.

Construction of an expression vector for efficient expression of the required gene in a host can be carried out by cloning a nucleic acid molecule according to the invention, in particular an appropriate DNA or cDNA, into an expression vector which is compatible with an appropriate host. A suitable host is, preferably, E. coli, preferably a derivative of the E. coli strain K12, for example a strain such as E. coli W3110 (ATCC 27325), JM103 (C. Yanish-Perron et al., Gene 33 (1985), 103–109), JM109 (C. Yanish-Perron et al., 1985, ibid.), JM83 (C. Yanish-Perron et al., 1985, ibid.), HB101 (J. Sambrook et al., 1989, ibid.), and C600 (J. Sambrook et al., 1989, ibid.). Examples of suitable expression vectors are vectors, in particular plasmids, for example pKK223–2 (GenBank Acc. No. M77749), pK19 (R. D. Pridmore, Gene 56 (1987), 309–312), or pPLa832 (E. L. Winnacker, Gene and Klone, Verlag Chemie, Weinheim 1984/1985), which comprise a suitable promoter functioning in a host (for example Lac, Tac, Trc, Trp or PL) and a ribosome binding site (RBS, Shine-Dalgamo (SD) sequence), or ATG vectors (for example pKK233–2, obtainable from Pharmacia), which additionally comprise the translation start codon ATG. Introduction of the expression vector into a suitable host results in a microorganism which effectively expresses cephalosporin acetylesterase.

The recombinant expression vector obtained in this way is introduced by transformation into an appropriate host, producing a novel host strain producing cephalosporin acetylesterase.

The transformed cells are cultivated under suitable conditions under which expression of CAE is brought about. After expression of the CAE has taken place, the host cells are disrupted. The expressed cephalosporin acetylesterase can be purified by a conventional purification process, for example by centrifugation, column chromatography and the like or a suitable combination thereof. An alternative possibility is also, for example, to employ cell supernatents or suspensions of disrupted host cells which contain the expressed CAE subsequently.

The expressed recombinant CAE can also be purified by affinity chromatography using immobilized antibodies which themselves can be obtained in a manner known per se using CAE isolated from B. subtilis ATCC 6633 (DSM 1 1909) as antigen.

The recombinantly prepared CAE can be immobilized on solid supports, which is a great advantage especially for industrial use. The use of solid catalysts produced in this way presents great economic advantages in industrial use.

The recombinant CAE is used according to the invention in a process for preparing 3-deacetylcephalosporin compounds and subsequently for preparing semisynthetic cephalosporin compounds, in which case the acetyl radical of the acetoxymethyl group of cephalosporin compounds which have an acetoxymethyl group in position 3 is cleaved off by the CAE.

A process according to the invention of this type comprises the following steps:

(i) Conversion of a cephalosporin compound which has an acetoxymethyl group in position 3 using a recombinantly prepared cephalosporin acetylesterase from B. subtilis ATCC 6633 (DSM 11909), which is employed in free form or in immobilized form; and, where appropriate, (ii) isolation of the 3-deacetylcephalosporin compound formed.

In order subsequently to prepare further cephalosporin compounds as final products, the 3-deacetylcephalosporin compound which has been formed is isolated, further purified where appropriate, and subsequently converted into the required final product. Alternatively, the resulting reaction solution containing 3-deacetylcephalosporin compound formed is subsequently converted in order finally to obtain the required final product.

The cephalosporin compound which is employed in the process according to the invention and has acetoxymethyl group in position 3 is, in particular, 7-aminocephalosporanic acid or a 7-acyl derivative. One example of such a derivative is cephalosporin C.

Thus, according to the invention, for example 7-aminocephalosporanic acid is converted into 7-amino-3-deacetylcephalosporanic acid and cephalosporin C is converted into 3-deacetylcephalosporin C.

The reaction conditions are familiar to the skilled person and correspond to those for the conversion with native cephalosporin acetylesterase (see, e.g., J. Konecny, Enzyme Engineering 4 (1978), pp. 253–259).

The full contents of the texts mentioned are incorporated herein by reference.

The present invention is illustrated in detail by the following examples but is not restricted thereto. In particular, the examples relate to preferred embodiments of the present invention.

The materials mentioned herein, such as other enzymes and reagents, are familiar to the skilled person, commercially available and can be used in accordance with the manufacturer's instructions.

EXAMPLES

Example 1

Fermentation and Isolation of the Cephalosporin Acetylesterase (CAE) from *B. subtilis* ATCC 6633 (DSM 11909)

CAE from the *Bacillus subtilis* strain ATCC 6633 (DSM 11909) is fermented as described by J. Konecny et al. (1977), isolated and purified to homogeneity according to polyacrylamide gel electrophoresis as described by H. R. Maurer, in: Disk Electrophoresis, Walter de Gruyter Verlag, Berlin (1971). After the final ion exchange step, the CAE solution is lyophilized and stored at −20° C. until characterized further.

Example 2

Production of antibodies Directed Against the CAE from *B. subtilis* ATCC 6633 (DSM 11909)

A polyclonal antibody against CAE from ATCC 6633 (DSM 11909) is produced by immunizing rabbits by conventional immunization protocols using the CAE prepared as in Example 1. For example, a rabbit receives 4 injections of 40 mg of CAE after 0, 2, 4 and 8 weeks. After 11 weeks, the serum enriched in specific antibodies is isolated. Before use, the polyclonal antibodies are purified by affinity chromatography (protein A column).

Example 3

DNA Isolation from *B. subtilis* ATCC 6633 (DSM 11909)

*B. subtilis* ATCC 6633 (DSM 11909) is cultured overnight (in LB medium, 250 ml, 200 rpm, 30° C). The cells are harvested by centrifugation, washed in salt/EDTA (150 mM NaCl, 100 mM EDTA, pH 8.0) and suspended in 10 ml of salt/EDTA (150 mM NaCl, 100 mM EDTA, pH 8.0). After addition of about 10 mg of lysozyme (possibly also addition of RNase, about 1 mg), incubation is carried out at 30° C. with cautious stirring until lysis starts, and then the mixture is cooled in an ice bath and 10 ml of Tris/SDS are added (100 mM Tris, 100 mM NaCl, 1% SDS, pH 9.0). After about 3–5 min, about 2 mg of proteinase K are added with cautious mixing, and the mixture is warmed at 40° C. for about 40 min. The lysate is treated twice with about 10 ml of Tris/SDS-saturated phenol each time and once with 1/1 phenol/chloroform, the aqueous phase is aspirated off, and 1/10 of the volume of 3 M sodium acetate is added and mixed. After overlaying with 2 volumes of absolute ethanol (precooled to −20° C.), the fine DNA threads are isolated at the phase boundary. The DNA is dissolved in water.

An alternative possibility to this classical method is also to use a commercially obtainable kit, for example the Qiagen DNA isolation kit.

Example 4

Cloning of the CAE Gene in pK19 and Sequencing

A PCR is carried out with genomic DNA obtained from *B. subtilis* ATCC 6633 (DSM 11909) as in Example 2, using the oligonucleotide primers EST12 (SEQ ID NO. 3) and EST13 (SEQ ID NO. 4), which are depicted below, and using Pwo polymerase (obtainable from Boehringer Mannheim).

Oligonucleotide EST12:Length: 27mer

5'-atg caa cta ttc gat ctg ccg ctc gac - 3' (SEQ ID NO. 3) ("Forwards" primer, starting with the ATG start codon)

Oligonucleotide EST13:Length: 27mer 5'-tca gcc ttt aag atg ctg ctt aaa gaa - 3' (SEQ ID NO. 4) (Reverse primer, starting with the TGA stop codon)

A DNA fragment about 1 kb in size can be detected after analysis by agarose gel electrophoresis. The fragment is eluted from the agarose gel and ligated into the cloning vector pK19 (R. D. Pridmore, Gene 56 (1987), 309–312) which has been cut with the restriction endonuclease SmaI. The ligation mixture is transformed into *E. coli* K12 JM83 (C. Yanish-Perron et al., Gene 33 (1985), 103–109) by electroporation. Plasmid clones are detected as colonies after incubation on LB medium with 50 mg/l kanamycin at 37° C. for about 16 h. The correct clones are characterized by plasmid isolation and restriction analysis, the insert being found in both orientations. The corresponding plasmids are called pKCE1 and pKCE2.

Four independently isolated clones are selected, the corresponding plasmid DNA is isolated therefrom, and the insert is completely sequenced in each case. All four inserts are identical in nucleotide sequence in all positions. The sequence of the fragment 957 bp in size is depicted in Annex 2 (SEQ ID NO. 2).

Translation of the sequence results in a derived amino acid sequence of 318 amino acids as depicted in Annex 1 (SEQ ID NO. 1).

Example 5

Expression with pKCE1

The two plasmids pKCE1 and pKCE2 in which the orientation of the CAE gene differs are transformed into the host strain *E. coli* K12 JM83 (see above). The gene in pKCE1 is in the same orientation as the lacZ promoter present on pK19 in front of the cloning site; the gene has the opposite orientation in pKCE2.

CAE expression is detected by Western blot using antibodies obtained as in Example 2. For this purpose, the strains are cultured overnight in a preculture (LB medium with 50 µg/ml kanamycin) at 37° C. The main culture is inoculated with 40 ml of preculture in 2l and cultivated in production medium (per liter: 20 g of casein hydrolysate (Difco), 10 g of yeast extract (Difco), 6 g of $Na_2HPO_4$, 3 g of $NaH_2PO_4$, 0.5 g of NaCl, 1 g of $NH_4Cl$, 2 mM $MgSO_4$ and 0.1 mM $CaCl_2$ and kanamycin (50 µg/ml)) at 37° C. for 10 hours. No inducer is added. The fermentation takes place in the smallest laboratory fermenter at a stirring speed of 400 rpm and an aeration rate of 2 Nl/min.

The fermentation broth is centrifuged. Two grams of the cell pellet are resuspended in 18 ml of 200 mM phosphate buffer, and the cells are disrupted under high pressure in a French Press Lab40 (twice at 700 bar). After centrifugation, the supernatant and the precipitate are each analysed by Western blot. The SDS page is carried out with NuPage® precast gels (supplied by Novex) according to the Novex instructions for use. The blot is carried out by the method of R. Westermeier, Electrophoresis in Practice—Second Edition, Verlag VCH, Heidelberg, (1990), using the semidry technique. The immunological staining is carried out by means of alkaline phosphatase-coupled goat anti-rabbit antibody (supplied by Sigma, Cat. No. A-3687) according to the Sigma instructions for use.

After pKCE1 fermentation, CAE expression can be detected by Western blot, whereas the Western blot of pKCE2 shows no expression. This proves that the CAE gene in pKCE1 is under the control of the lacZ promoter.

Example 6

Determination of the Cephalosporin Acetylesterase Activity

The following assays can be used to determine the enzymatic activity of recombinant CAE.
(a) Photometric Activity Determination CAE catalyses the hydrolysis of p-nitrophenyl acetate to p-nitrophenol. For this assay, 50 µl of CAE solution are mixed with 750 µl of 0.1 M phosphate buffer (pH 7.0) and 200 µl of 1 mM p-NPA solution at a constant 37° C. The production of p-nitrophenol is followed by measuring the extinction at 400 nm ($\epsilon 400nm=9.27$ $cm^2/\mu mol$). One activity unit (1 U) corresponds to the conversion of 1 µmol of p-NPA per minute.
(b) Titrimetric Activity Determination The CAE activity is measured by cleavage of cephalosporin C (CC) to 3-deacetylcephalosporin C (3-DA-CC) by titrimetric measurement of the liberated acetic acid. The acetic acid is titrated against NaOH at constant pH. The CAE activity is determined from the NaOH consumption. The determination is done using, for example, a pH-stat system with Metrohm components (Metrohm 632 +pH meter, Metrohm dispenser). The enzymatic reaction is carried out in a 50 ml liquid-thermostated jacketed vessel.

One active unit (1 unit, 1 U) corresponds to the conversion of 1 µmol of cephalosporin C Na salt per minute under the following conditions: 75 mM cephalosporin C Na salt; 5 mM phosphate buffer; pH 8.0; 25° C.; titration with 0.5 M NaOH. After the phosphate buffer has been introduced into the jacketed vessel, cephalosporin C Na salt is added. The titration with NaOH is started, keeping the pH constant. In this phase, NaOH is consumed by the self cleavage (without enzyme) of cephalosporin C. The self-cleavage of cephalosporin C is observed for about 10 min, then CAE is added, and the consumption of sodium hydroxide solution is measured for about 20 min. The CAE activity is determined from the difference between the NaOH consumption during the self cleavage and the NaOH consumption during the enzymatic reaction.

Example 7

Characterization of the CAE Expressed by pKCE1

The activity of the supernatant is determined by titrimetry as in Example 6. The supernatant is evaporated by means of an infrared drier/balance, and the activity is related to the weight of dry matter, The result is accordingly 455 U per gram of dry matter.

Example 8

Immobilization of the CAE from B. subtilis ATCC 6633 (DSM 1 1909)

a) 25 mg of purified CAE are dissolved in 20 ml of 0.5 M $Na_2SO_4$, pH 7.5, in a 100 ml polypropylene vessel and, after addition of 0.5 g of Eupergit C, rotated at RT for 18 h. Then Eupergit C is filtered off and washed with 40 ml of water in several portions. The aqueous washings are used for further immobilization on Eupergit C (2 g of Eupergit C, RT, 66 h).

b) As an alternative, 1 ml Sedifloc® CL 900–18/40 is added to a cell homogenate of the recombinant E. coli K12 JM83 pKCE1 yielded from 2 g wet cell pellet (15100 U CCAE) in 50 ml of 50 mM phosphate buffer pH 7.0. The suspension is adjusted to pH 5.2 with acetic acid and under stirring heated to 40° C. for 1 hour. The coagulation suspension is cooled to 10° C. and stirred for one additional hour. By centrifugation a clear supernatant is received which is readjusted to pH 7.5. This purified CCAE containing solution (12080 U CCAE =100%) is mixed with 8.4 g Eupergit® C and 50 ml 1 M sodium phosphate buffer, pH 7.0. After 64 hours of slightly stirring at room temperature the carrier was separated from the solution and washed with water. Finally 672 U/g d.w. and 5630 $U_{101}$ of immobilized CCAE activity were found.

Example 9

Hydrolysis of 7-aminocephalosporanic Acid (7-ACA) to 3-deacetylcephalosporanic Acid (HACA)

CAE is immobilized as described in example 8.b. 1g d.w. of the catalyst is incubated under stirring in 100 ml 7-ACA solution (100 mM 7-ACA, 80 mM borate, pH 8.0; automatic titration with 2 N ammonia) at room temperature. By HPLC analysis it is determined that after 90 min 7-ACA is quantitatively transformed to HACA. The sum of side products is less than 1 mM. The activity of the recovered enzyme is after use 665 U/g d.w.

Example 10

Hydrolysis of Cephalosporin C to 3-deacetylcephalosporin C

CAE is immobilized as described in example 8.b and used to hydrolyze Cephalosporin C. 1 g d.w. of the catalyst is incubated under stirring in 100 ml Cephalosporin C solution (100 mM Cephalosporin C, 80 mM borate, pH 8.0; automatic titration with 2 N ammonia) at roomtemperature. By HPLC analysis it is determined that after 90 min Ceph C was quantitatively transformed to 3-Deacetyl-cephalosporin C. The sum of side products is less than 1 mM. The activity of the recovered enzyme is after use 670 U/g d.w.

Deposition of Microorganisms

The *Bacillus subtilis* strain ATCC 6633 mentioned in the present application was deposited on Dec. 22, 1997 at the DSMZ—Deutsche Sammlung von Mikroorganismen und Zelikulturen GmbH, Mascheroder Weg 1 b, D-38124 Braunschweig, in accordance with the Budapest Treaty and was assigned deposition number DSM 1 1909.

```
MQLFDLPLDQLQTYKPEKTTPNDFSEFWKSSLDELAKVKAAPDLQLVDYPAD    Annex 1: SEQ ID NO. 1

GVKVYRLTYKSFGNARITGWYAVPDKEGPHPAIVKYHGYNASYDGEIHEMVN

WALHGYAAFGMLVRGQQSSEDTSISPHGHALGWMTKGILDKDTYYYRGVYLD

AVRALEVISSFDEVDETRIGVTGGSQGGGLTIAAAALSDIPKAAVADYPYLS

NFERAIDVALEQPYLEINSFFRRNGSPETEEKAMKTLSYFDIMNLADRVKVP

VLMSIGLIDKVTPPSTVFAAYNHLETEKELKVYRYFGHEYIPAFQTEKLAFF

KQHLKG
```

```
  1 ATGCAACTAT TCGATCTGCC GCTCGACCAA TTGCAAACGT ATAAGCCTGA    Annex 2: SEQ ID NO. 2:
 51 AAAAACAACA CCGAACGATT TTTCTGAGTT TTGGAAATCG TCTTTGGACG
101 AACTTGCGAA AGTCAAAGCA GCACCTGATT TACAGCTGGT TGATTATCCT
151 GCTGATGGAG TCAAGGTGTA CCGCCTCACA TATAAAAGCT TCGGAAACGC
201 CCGCATTACC GGATGGTACG CAGTGCCTGA CAAGGAAGGA CCGCATCCGG
251 CGATCGTCAA ATATCATGGC TACAACGCTA GCTATGACGG TGAGATTCAT
301 GAAATGGTAA ACTGGGCGCT CCACGGTTAC GCCGCATTCG GCATGCTAGT
351 CCGCGGCCAG CAGAGCAGCG AGGATACGAG TATTTCTCCA CATGGCCATG
401 CTTTGGGCTG GATGACGAAA GGAATCCTTG ATAAAGATAC ATACTATTAC
451 CGGGGCGTTT ATTTGGACGC TGTCCGCGCG CTTGAGGTCA TCAGCAGCTT
501 TGACGAAGTT GACGAAACAA GAATCGGTGT GACAGGCGGA AGCCAAGGAG
551 GCGGCTTAAC CATTGCCGCA GCCGCTCTGT CAGACATTCC AAAAGCCGCG
601 GTTGCCGATT ATCCTTATTT AAGCAACTTT GAACGGGCCA TTGATGTGGC
651 GCTTGAACAG CCGTACCTTG AAATCAATTC CTTCTTTAGA AGAAATGGAA
701 GCCCGGAAAC GGAAGAGAAG GCGATGAAGA CACTTTCATA TTTCGATATT
751 ATGAATCTCG CTGACCGAGT GAAGGTCCCT GTCCTGATGT CGATCGGTCT
801 GATTGACAAG GTCACGCCGC CGTCCACCGT GTTTGCCGCA TACAACCACT
851 TGGAGACAGA GAAAGAGCTC AAAGTGTACC GCTACTTCGG GCATGAGTAT
901 ATCCCTGCCT TCAAACAGA AAAACTTGCT TTCTTTAAGC AGCATCTTAA
951 AGGCTGA
```

What is claimed is:

1. A nucleic acid molecule which codes for the cephalosporin acetylesterase from B subtilis ATCC 6633 (DSM 11909), wherein the cephalosporin acetylesterase has the amino acid sequence shown in SEQ ID NO: 1.

2. The nucleic acid molecule according to claim 1 comprising a base sequence as shown in SEQ ID NO: 2.

3. A vector which is compatible with a predetermined host cell, comprising a nucleic acid molecule according to claim 1.

4. The vector according to claim 3, where the vector is an expression vector.

5. A host cell comprising a vector according to claim 3.

6. A process for the recombinant production of the cephalosporin acetylesterase from *B. subtilis* ATCC 6633 (DSM 11909), comprising
(i) cultivating, under conditions which are suitable for bringing about the expression of the cephalosporin acetylesterase, a host cell which is transformed with a vector according to claim 4, and thereafter
(ii) isolating the expressed cephalosporin acetylesterase if desired.

7. A process for the production of a 3-deacetylcephalosporin compound, comprising
(i) converting a cephalosporin compound which has an acetoxymethyl group in position 3 using a recombinantly prepared cephalosporin acetylesterase from *B. subtilis* ATCC 6633 (DSM 11909), wherein the cephalosporin acetylesterase has the amino acid sequence shown in SEQ ID NO: 1 and which is employed in free form or in immobilized form; and therafter (ii) isolating the 3-deacetylcephalosporin compound formed if desired.

8. The process according to claim 7, where the cephalosporin compound which has an acetoxymethyl group in position 3 is 7-aminocephalosporanic acid or a 7-acyl derivative thereof.

9. The process according to claim 8, where the 7-acyl derivative of 7-aminocephalosporanic acid is cephalosporin C.

* * * * *

UNITED STATES PATENT AND TRADEMARK OFFICE
CERTIFICATE OF CORRECTION

PATENT NO. : 6,465,233 B1
DATED : October 15, 2002
INVENTOR(S) : Knauseder et al.

It is certified that error appears in the above-identified patent and that said Letters Patent is hereby corrected as shown below:

<u>Title page,</u>
Item [30], Foreign Application Priority Data should read:

-- [30] Foreign Application Priority Data
  Jan. 28, 1998   (AT)...................A129/98 --

Signed and Sealed this

Twelfth Day of August, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 318
<212> TYPE: PRT
<213> ORGANISM: Bacillus subtilis

<400> SEQUENCE: 1

```
Met Gln Leu Phe Asp Leu Pro Leu Asp Gln Leu Gln Thr Tyr Lys Pro
 1               5                  10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
 65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315
```

<210> SEQ ID NO 2
<211> LENGTH: 957
<212> TYPE: DNA
<213> ORGANISM: Bacillus subtilis

<400> SEQUENCE: 2

```
                                   -continued atgcaactat tcgatctgcc gctcgaccaa ttgcaaacgt ataagcctga aaaaacaaca      60
ccgaacgatt tttctgagtt ttggaaatcg tctttggacg aacttgcgaa agtcaaagca     120
gcacctgatt tacagctggt tgattatcct gctgatggag tcaaggtgta ccgcctcaca     180
tataaaagct tcggaaacgc ccgcattacc ggatggtacg cagtgcctga caaggaagga     240
ccgcatccgg cgatcgtcaa atatcatggc tacaacgcta gctatgacgg tgagattcat     300
gaaatggtaa actgggcgct ccacggttac gccgcattcg gcatgctagt ccgcggccag     360
cagagcagcg aggatacgag tatttctcca catggccatg ctttgggctg gatgacgaaa     420
ggaatccttg ataaagatac atactattac cggggcgttt atttggacgc tgtccgcgcg     480
cttgaggtca tcagcagctt tgacgaagtt gacgaaacaa gaatcggtgt gacaggcgga     540
agccaaggag gcggcttaac cattgccgca gccgctctgt cagacattcc aaaagccgcg     600
gttgccgatt atccttattt aagcaacttt gaacgggcca ttgatgtggc gcttgaacag     660
ccgtaccttg aaatcaattc cttctttaga agaaatggaa gcccggaaac ggaagagaag     720
gcgatgaaga cactttcata tttcgatatt atgaatctcg ctgaccgagt gaaggtccct     780
gtcctgatgt cgatcggtct gattgacaag gtcacgccgc cgtccaccgt gtttgccgca     840
tacaaccact tggagacaga gaaagagctc aaagtgtacc gctacttcgg gcatgagtat     900
atccctgcct ttcaaacaga aaaacttgct ttctttaagc agcatcttaa aggctga       957

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
atgcaactat tcgatctgcc gctcgac                                          27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
tcagccttta agatgctgct taaagaa                                          27
```